United States Patent [19]

Kny

[11] 4,055,584
[45] Oct. 25, 1977

[54] PROCESS FOR THE PRODUCTION OF BETA-CHLOROETHYLTRICHLOROSILANE

[75] Inventor: Hermann Kny, Fullinsdorf, Switzerland

[73] Assignee: Ciba-Geigy Corporation, Ardsley, N.Y.

[21] Appl. No.: 722,858

[22] Filed: Sept. 10, 1976

[51] Int. Cl.$^2$ .............................. C07F 7/08; C07F 7/12
[52] U.S. Cl. ............................................... 260/448.2 E
[58] Field of Search ................................... 260/448.2 E

[56] References Cited

U.S. PATENT DOCUMENTS 3,801,614  4/1974  Lohmann et al. ............ 260/448.2 E
3,933,881  1/1976  Föry et al. .................... 260/448.2 E Primary Examiner—Paul F. Shaver
Attorney, Agent, or Firm—Karl F. Jorda

[57] ABSTRACT

An improvement in the production of β-chloroethyltrichlorosilane by reacting hydrogen chloride with vinyl trichlorosilane in the presence of aluminum chloride at elevated pressure at temperatures between 0° and 90° C is disclosed, which comprises using the aluminium chloride which remains in the reaction vessel after separating off the β-chloroethyltrichlorosilane, and which still contains β-chloroethyltrichlorosilane, directly for the next reaction.

4 Claims, No Drawings

PROCESS FOR THE PRODUCTION OF BETA-CHLOROETHYLTRICHLOROSILANE

The present invention provides an improved process for the production of β-chloroethyltrichlorosilane by reacting vinyl trichlorosilane with hydrogen chloride.

According to the process described in U.S. Pat. No. 3,801,614, β-chloroethyltrichlorosilane is prepared by reacting hydrogen chloride with vinyl trichlorosilane in the presence of aluminium chloride at elevated pressure and temperatures between 0° and 90° C. The yields obtained in this process are up to 95% of theory. The losses in yield that occur even under very advantageous process conditions are primarily attributable to the fact that the end product cannot be separated from the catalyst by distillation completely.

The present invention therefore has for its object to overcome the difficulties involved in carrying out the known process and to provide a process which enables the β-chloroethyltrichlorosilane formed during the reaction of hydrogen chloride with vinyl trichlorosilane to be obtained in virtually quantitative yield.

It has been found that the β-chloroethyltrichlorosilane formed by the addition of hydrogen chloride to vinyl trichlorosilane can be isolated from the reaction mixture in virtually quantitative yield by using the aluminium chloride which remains in the reaction vessel after separating off the β-chloroethyltrichlorosilane by distillation, and which still contains β-chloroethyltrichlorosilane, directly in for the next reaction. In the present process, β-chloroethyltrichlorosilane is distilled off after each reaction in such an amount that the residue constitutes a broth which is still stirrable. In actual practice, the procedure is that, depending on the amount of aluminium chloride used and while maintaining the original size of the batch, about 80 to 90% of theory of β-chloroethyltrichlorosilane is distilled off after the first reaction, which is carried out in the presence of aluminium chloride, then fresh vinyl trichlorosilane and hydrogen chloride are added and, when the further reactions are complete, the amount of β-chloroethyltrichlorosilane corresponding to the newly added amount of vinyl trichlorosilane is distilled off after each reaction.

The overpressure to be applied can vary within a wide range, as in the process described in U.S. Pat. No. 3,801,614. It can be up to 30 bar and the reaction temperatures can be between 0° and 90° C. In connection with the reuse of the catalyst proposed according to the invention, it is advantageous to carry out the process at an overpressure between 0.5 and 3 bar and a temperature between 20° and 40° C. The amount of aluminium chloride can also vary within a wide range and be from 1 to 15 percent by weight, referred to the amount of vinyl trichlorosilane used. In particular, the addition of 3 to 6 percent by weight of aluminium chloride, referred to the amount of vinyl trichlorosilane used, has proved advantageous.

The procedure of this invention makes it possible to isolate the β-chloroethyltrichlorosilane in virtually quantitative yield. In practice, this results in a yield of 100%. Since losses causes by product adhering to the catalyst are eliminated, it is possible to use larger amounts of catalyst, which makes a more rapid reaction possible. Moreover, the repeated use of the catalyst results in less catalyst being used on the whole than if a specific amount were used once. In addition, less work is involved, since the reaction vessel does not have to be cleaned after each batch and it is charged only with products in liquid and gaseous form. The reduced amount of aluminium chloride is also advantageous from the ecological point of view, because the effluents contain less aluminium. The risks involved in the decomposition of the residue are also reduced, since in this case an explosive gas mixture is formed.

The invention is illustrated in more detail by the following Example.

EXAMPLE

A 2.5 liter glass pressure reactor is charged with 1.62 kg (10 moles) of vinyl trichlorosilane and 75 g of aluminium chloride. With stirring, hydrogen chloride is then forced in until an internal pressure of 1.5 bar is reached. The temperatures rises initially from 20°/25° to 40° C and is kept thereat by cooling. The uptake of hydrogen (440 g) is complete after 4 hours. Subsequently 1.7 kg (86% of theory) is distilled off at 16 to 18 bar. A further 1.62 kg (10 moles) of vinyl trichlorosilane is added to the residue, which is in the form of a stirrable broth, and, as described above, hydrogen chloride is forced in until an internal pressure of 1.5 bar is reached and reacted with the vinyl trichlorosilane at 40° C. When the reaction is complete, 1.96 kg (98% of theory) of β-chloroethyltrichlorosilane is distilled off from the reaction mixture, whereupon a stirrable broth again remains as residue. A further 1.62 kg of vinyl trichlorosilane is added to this residue and hydrogen chloride is force in until an internal pressure of 1.5 bar is reached and the addition is effected as described above.

As the experiments carried out have shown, the catalyst can be used at least 10 times in the described manner without losing its activity.

What is claimed is:

1. In a process for the production of β-chloroethyltrichlorosilane by reacting hydrogen chloride with vinyl trichlorosilane in the presence of aluminium chloride at elevated pressure at temperature between 0° and 90° C, the improvement which comprises using the aluminium chloride which remains in the reaction vessel after separating off the β-chloroethyltrichlorosilane by distillation, and which still contains β-chloroethyltrichlorosilane, directly in the next reaction, provided that β-chloroethyltrichlorosilane is distilled off after each reaction in such an amount that the residue constitutes a still stirrable broth.

2. A process according to claim 1, wherein 80 to 90% of theory of β-chloroethyltrichlorosilane is distilled off after the first reaction in the presence of fresh aluminium chloride, while maintaining the original size of the batch, fresh vinyl trichlorosilane and hydrogen chloride are added, and, after completion of the further reactions, the amount of β-chloroethyltrichlorosilane corresponding to the freshly used amount of vinyl trichlorosilane is distilled off after each reaction.

3. A process according to claim 1, wherein the reaction is carried out at an overpressure of 0.5 to 3 bar and a temperature of 20° to 40° C.

4. A process according to claim 1, wherein the reaction is carried out in the presence of 3 to 6 percent by weight of aluminium chloride, referred to the amount of vinyl trichlorosilane used.

* * * * *